United States Patent
Zhou et al.

(10) Patent No.: US 8,628,752 B2
(45) Date of Patent: Jan. 14, 2014

(54) METHODS OF IDENTIFYING HSP90 INHIBITORS WITH LESS OCULAR TOXICITY

(71) Applicant: Synta Pharmaceuticals Corp., Lexington, MA (US)

(72) Inventors: Dan Zhou, Lexington, MA (US); Takayo Inoue, Malden, MA (US)

(*) Notice: Subject to any disclaimer, the term of this patent is extended or adjusted under 35 U.S.C. 154(b) by 0 days.

(21) Appl. No.: 13/662,048

(22) Filed: Oct. 26, 2012

(65) Prior Publication Data

US 2013/0109045 A1     May 2, 2013

Related U.S. Application Data

(60) Provisional application No. 61/552,779, filed on Oct. 28, 2011.

(51) Int. Cl.
    *A61K 49/00*      (2006.01)

(52) U.S. Cl.
    USPC ........................................ 424/9.2; 435/40.52

(58) Field of Classification Search
    USPC ............................................................ 424/9.2
    See application file for complete search history.

(56) References Cited

PUBLICATIONS

Infante et al. A Phase I Dose-Escalation Study of the Oral Heat Shock Protein 90 Inhibitor PF-04929113 (SNX5422) and Its Associated Ocular Toxicity; Presented at the 22nd EORTC-NCI-AACR Symposium on Molecular Targets and Cancer Therapeutics, Berlin, Germany, Nov. 16-19, 2010. downloaded from http://www.hsp90central.com.*

Zhang et al. Pharmacokinetic and Toxicity Study of Intravitreal Erythropoietin in Rabbits; Acta Pharmacologica Sinica, vol. 29, No. 11 (2008) pp. 1383-1390.*

* cited by examiner

*Primary Examiner* — Susan Hanley
*Assistant Examiner* — Paul Martin
(74) *Attorney, Agent, or Firm* — McCarter & English, LLP; Steven G. Davis; Mei Bai (57) ABSTRACT

Provided is a method of identifying Hsp90 inhibitors with substantially less ocular toxicity or with substantially improved ocular toxicity profile. The method comprises measuring the respective concentrations of an Hsp90 inhibitor in the retina and plasma at certain time points following the administration of the Hsp90 inhibitor in a subject, and determining the concentration ratio of the Hsp90 inhibitor between retina and plasma, where a certain ratio is indicative that the Hsp90 inhibitor has substantially less ocular toxicity. The method also includes identifying an Hsp90 inhibitor with substantially less ocular toxicity, or with a substantially improved ocular toxicity profile, by determining the elimination rate of the Hsp90 inhibitor from the retina following administration of the Hsp90 inhibitor, where a certain elimination rate is indicative that the Hsp90 inhibitor will induce substantially less ocular toxicity.

8 Claims, 5 Drawing Sheets

METHODS OF IDENTIFYING HSP90 INHIBITORS WITH LESS OCULAR TOXICITY

CROSS-REFERENCE TO RELATED PATENTS

This application claims the benefit of priority to U.S. Provisional Patent Application No. 61/552,779, filed on Oct. 28, 2011. The contents of the above application are incorporated herein by reference in its entirety.

BACKGROUND OF THE INVENTION

Heat shock proteins (HSPs) are a class of chaperone proteins that are up-regulated in response to elevated temperature and other environmental stresses, such as ultraviolet light, nutrient deprivation and oxygen deprivation. HSPs act as chaperones to other cellular proteins (called client proteins), facilitate their proper folding and repair and aid in the refolding of misfolded client proteins. There are several known families of HSPs, each having its own set of client proteins. The Hsp90 family is one of the most abundant HSP families accounting for about 1-2% of proteins in a cell that is not under stress and increasing to about 4-6% in a cell under stress. Inhibition of Hsp90 results in the degradation of its client proteins via the ubiquitin proteasome pathway. Unlike other chaperone proteins, the client proteins of Hsp90 are mostly protein kinases or transcription factors involved in signal transduction, and a number of its client proteins have been shown to be involved in the progression of cancer. Because pharmacological inhibition of Hsp90 destabilizes client proteins, which leads to the degradation of these proteins, tumors are proposed to be more sensitive to the inhibition of Hsp90, as tumors are more dependent on the chaperone activity of Hsp90 than non-malignant cells. Since targeted inhibition of Hsp90 results in the simultaneous blockade of multiple oncogenic signaling pathways, it has emerged as an attractive strategy for the development of novel cancer therapeutics.

In addition to regulating a number of oncogenic client proteins, the Hsp90 molecular chaperone also controls the folding of key signaling molecules required to maintain normal cell function in many organs, including the retina. In human clinical trials, Hsp90 inhibition has been associated with visual disorders including blurred vision, flashes, delayed light/dark accommodation, and photophobia. These adverse effects (toxic effect or toxicological effect) involving injury to the retina may be attributable to photoreceptor degeneration and/or cell death, as previously reported in dogs following repeated doses of Hsp90 inhibitor PF-04929113 (a/k/a SNX-5422).

SUMMARY OF THE INVENTION

A method of predicting or identifying ocular toxicity or ocular toxicological effect of Hsp90 inhibitors is disclosed herein. In an embodiment, the method includes measuring the respective concentrations of an Hsp90 inhibitor in the retina and in plasma at certain time points following the administration of an effective amount of the Hsp90 inhibitor or a pharmaceutically acceptable salt or carrier thereof, determining the concentration ratio of the Hsp90 inhibitor between retina and plasma, wherein a certain ratio is indicative that the Hsp90 inhibitor has substantially less ocular toxicity or possesses an improved ocular toxicity profile.

In another embodiment, methods also include determining whether an Hsp90 inhibitor will induce ocular toxicity or visual disorder in vivo, by determining the concentration ratio of an Hsp90 inhibitor in retina and plasma following administration of the Hsp90 inhibitor to a subject, wherein a certain concentration ratio is indicative that administration of the Hsp90 inhibitor will likely have ocular toxicity in vivo. In an embodiment, a concentration ratio above 25, when measured at about 6 hours following administration of the Hsp90 inhibitor, is indicative that the Hsp90 inhibitor will likely induce ocular toxicity or visual disorder in vivo. In an embodiment, a concentration ratio of about 25 or below, when measured at about 6 hours following administration of the Hsp90 inhibitor, is indicative that the Hsp90 inhibitor will likely have substantially less ocular toxicity in vivo. In an embodiment, the subject is an animal. In an embodiment, the animal is a rat.

In an embodiment, the method also includes identifying an Hsp90 inhibitor with substantially less ocular toxicity or an improved ocular toxicity profile by measuring the elimination rate of an Hsp90 inhibitor from the retina at certain time points following the administration of an effective amount of the Hsp90 inhibitor or a pharmaceutically acceptable salt or carrier thereof in a subject, wherein a certain elimination rate is indicative that the Hsp90 inhibitor will likely have substantially less ocular toxicity. In an embodiment, an elimination rate of about 80% or above is indicative that administration of the Hsp90 inhibitor will likely have substantially less ocular toxicity. In an embodiment, an elimination rate of about 80% or more, measured at about half an hour and at about 6 hours following the administration of the Hsp90 inhibitor, is indicative that administration of the Hsp90 inhibitor will likely have substantially less ocular toxicity. In an embodiment, an elimination rate of below 80% is indicative that administration of the Hsp90 inhibitor will likely induce ocular toxicity or visual disorder. In an embodiment, an elimination rate of below 80% as measured at about half an hour and at about 6 hours following the administration of the Hsp90 inhibitor is indicative that administration of the Hsp90 inhibitor will likely induce ocular toxicity or visual disorder.

In an embodiment, the method also includes determining whether an Hsp90 inhibitor will have a toxicological effect on retinal tissue in vivo, by determining the elimination rate of an Hsp90 inhibitor from retina following the exposure of retinal tissue to an Hsp90 inhibitor, wherein a certain elimination rate of the Hsp90 inhibitor is indicative that administration of the Hsp90 inhibitor will have a toxicological effect on retinal tissue in vivo. In an embodiment, an elimination rate of about 80% or below is indicative that administration of the Hsp90 inhibitor will likely have a toxicological effect on retinal tissue. In an embodiment, an elimination rate of about 80% or above is indicative that administration of the Hsp90 inhibitor will likely have substantially less toxicological effect on retinal tissue.

BRIEF DESCRIPTION OF THE FIGURES

FIG. 4 shows the retina/plasma (R/P) drug concentration ratios for four Hsp90 inhibitors over time. AUY-922, the compound which displayed the highest R/P ratio at 6 h post-dose, produced the most severe ocular effects, whereas the lower R/P ratios of ganetespib and 17-AAG were associated with less risk of retinal damage. These data also suggest that high and prolonged drug exposure in the retina can enhance ocular toxicity, and that the retinal tissue distribution profiles play a critical role in Hsp90 inhibitor induced ocular toxicity in rats.

FIG. 5 shows that retinal elimination profiles correlate with the degree of observed ocular toxicity. 17-AAG and ganetespib, both of which showed an absence of ocular effects, were more rapidly eliminated from the retina compared to 17-DMAG and AUY-922. The longer retention time of 17-DMAG and AUY-922 within the retina likely contributed to their adverse effects within this tissue.

DETAILED DESCRIPTION OF THE INVENTION

Figure 1:
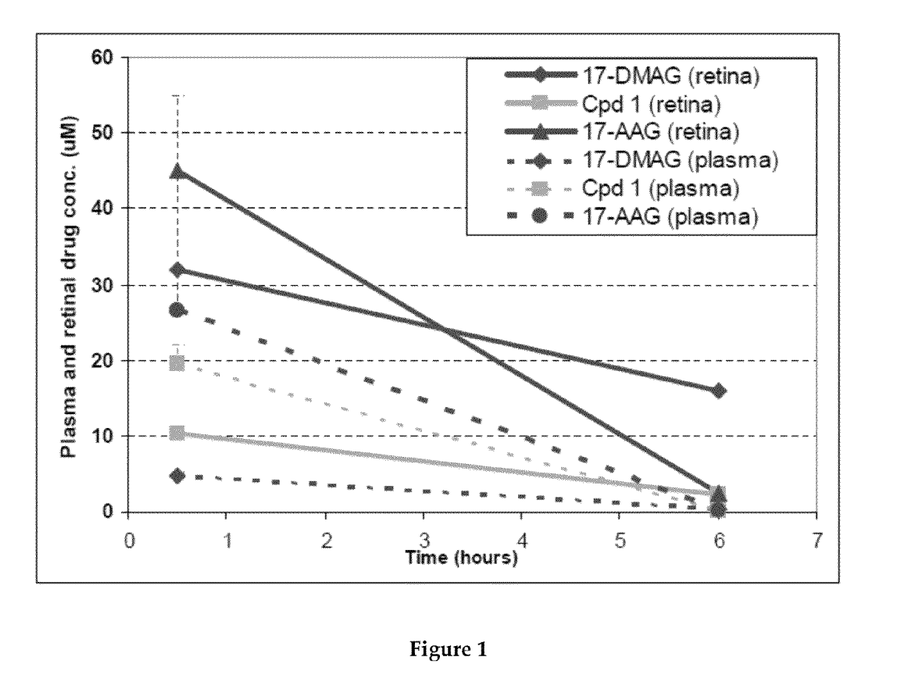
FIG. 1 shows plasma-retina drug concentrations in animals treated with 17-DMAG at 0.5 and 6 hrs, 17-AAG at 0.5 hr, and Compound 1 at 6 hrs, respectively.
Figure 2:
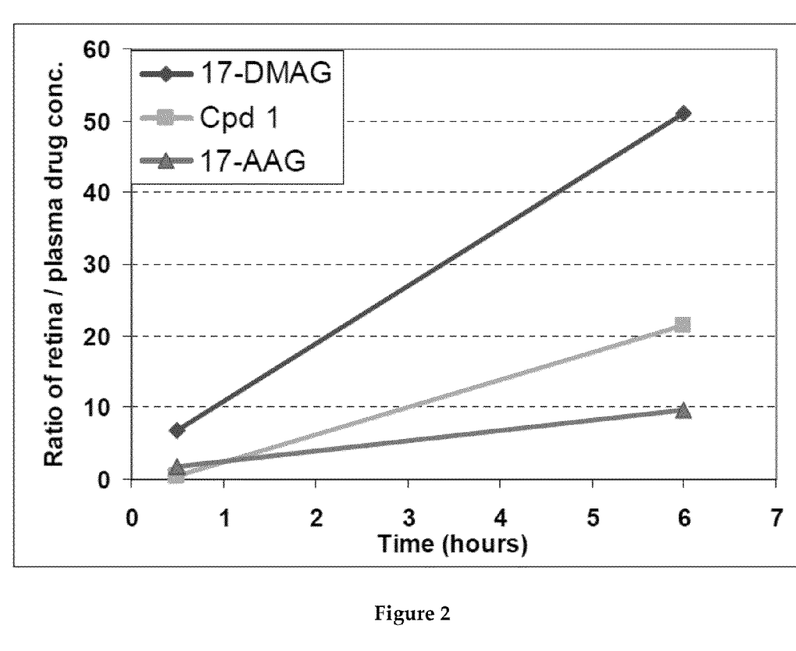
FIG. 2 shows that the Hsp90 inhibitors that displayed higher retina/plasma (R/P) ratio at 6 hours post-dose showed higher risk of producing ocular toxicity. These data also suggest that high and prolonged drug exposure in the retina can enhance ocular toxicity, and that the retinal tissue distribution profiles play an important role in Hsp90 inhibitor-induced ocular toxicity in rats.
Figure 3:
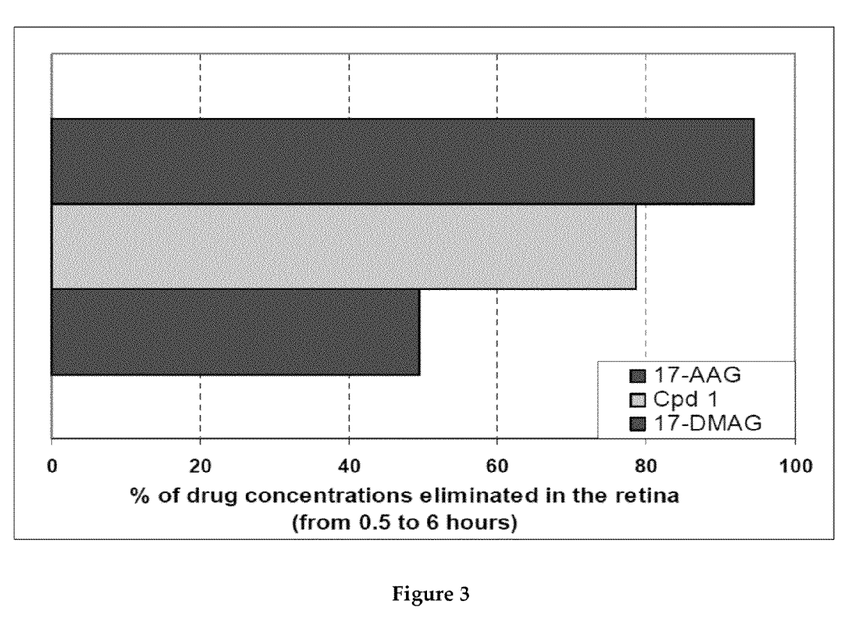
FIG. 3 shows that the tissue elimination profiles correlate well with ocular toxicity observed in rats. Mild or no ocular toxicity was observed in compound 1- and 17-AAG-treated animals. These compounds were more rapidly eliminated from the retina, in contrast to animals treated with 17-DMAG.
Figure 4:
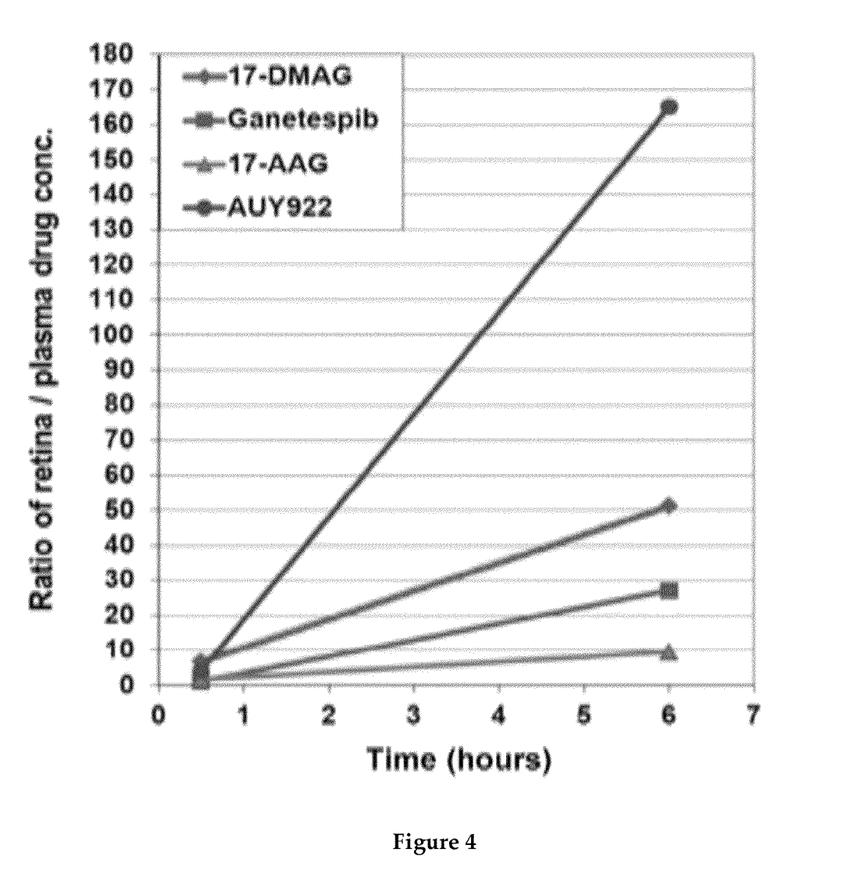
Figure 5:
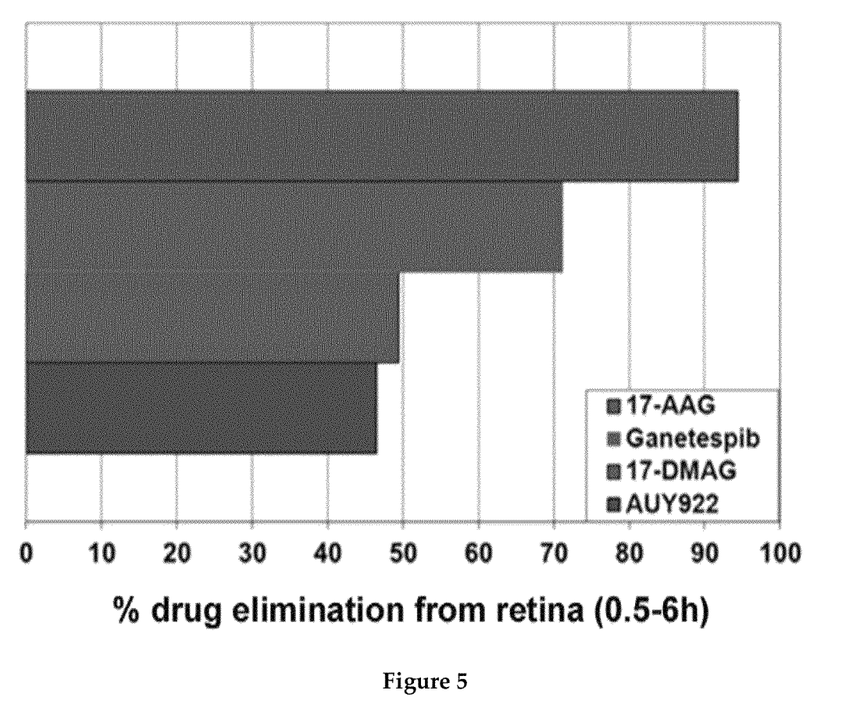

Unless otherwise specified, the below terms used herein are defined as follows:

The articles "a", "an" and "the" are used herein to refer to one or to more than one (i.e. to at least one) of the grammatical object of the article unless otherwise clearly indicated by contrast. By way of example, "an element" means one element or more than one element.

The term "including" is used herein to mean, and is used interchangeably with, the phrase "including but not limited to".

The term "or" is used herein to mean, and is used interchangeably with, the term "and/or," unless context clearly indicates otherwise.

The term "such as" is used herein to mean, and is used interchangeably, with the phrase "such as but not limited to".

The term "substantially" indicates the high level improvement which can be measured or observed or assayed using the techniques known in the art. Substantially less ocular toxicity substantially less ocular toxicology or substantially improved ocular toxicity profile or substantially improved ocular toxicology can be assayed or observed or determined through standard methods and will typically exceed at least about 50%, or at least about 60%, or preferably at least about 80% improvement, as compared with the Hsp90 inhibitors whose ocular toxicities are known.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

As used herein, the term "subject" refers to an animal (e.g., a bird such as a chicken, quail or turkey, or a mammal), preferably a mammal including a non-primate (e.g., a cow, pig, horse, sheep, rabbit, guinea pig, rat, cat, dog, and mouse) and a primate (e.g., a monkey, chimpanzee and a human). In one embodiment, the subject is a non-human animal such as a farm animal (e.g., a horse, cow, pig or sheep), or a pet (e.g., a dog, cat, guinea pig or rabbit). In another embodiment, the subject is a human.

As used herein, "Hsp90" includes each member of the family of heat shock proteins having a mass of about 90-kiloDaltons. For example, in humans the highly conserved Hsp90 family includes the cytosolic Hsp90α and Hsp90β isoforms, as well as GRP94, which is found in the endoplasmic reticulum, and HSP75/TRAP1, which is found in the mitochondrial matrix. Some exemplary Hsp90 inhibitors include geldanamycin derivatives, e.g., a benzoquinone or hygroquinone ansamycin HSP90 inhibitor such as IPI-493 (CAS No. 64202-81-9) and/or IPI-504 (CAS No. 857402-63-2); 17-AAG CAS No. 75747-14-7), BIIB-021 (CNF-2024, CAS No. 848695-25-0), BIIB-028, AUY-922 (also known as VER-49009, CAS No. 747412-49-3), SNX-5422 (CAS No. 908115-27-5), AT-13387 (CAS No. 912999-49-6), XL-888, MPC-3100, CU-0305, 17-DMAG (CAS No. 467214-21-7), CNF-1010 (CAS No. 946090-39-7), Macbecin (e.g., Macbecin I (CAS No. 73341-72-7), Macbecin II (CAS No. 73341-73-8)), CCT-018159 (CAS No. 171009-07-7), CCT-129397 (CAS No. 940289-57-6), PU-H71 (CAS No. 873436-91-0), or PF-04928473 (SNX-2112, CAS No. 945626-71-1), 1,2,4-triazole derivatives such as compound 1 ((4-isopropyl-6-(5-mercapto-4-(1-methyl-1H-indol-5-yl)-4H-1,2,4-triazol-3-yl)benzene-1,3-diol), and ganetespib (3-(2,4-dihydroxy-5-isopropyl-phenyl)-4-(1-methyl-indol-5-yl)-5-hydroxy-[1,2,4]triazole).

As used herein, the term "pharmaceutically acceptable salt" refers to a salt prepared from a compound having an acidic functional group, such as a carboxylic acid functional group, and a pharmaceutically acceptable inorganic or organic base. Suitable bases include hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N, N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like. The term "pharmaceutically acceptable salt" also refers to a salt prepared from a compound having a basic functional group, such as an amine functional group, and a pharmaceutically acceptable inorganic or organic acid. Suitable acids include hydrogen sulfate, citric acid, acetic acid, oxalic acid, hydrochloric acid (HCl), hydrogen bromide (HBr), hydrogen iodide (HI), nitric acid, hydrogen bisulfide, phosphoric acid, isonicotinic acid, oleic acid, tannic acid, pantothenic acid, saccharic acid, lactic acid, salicylic acid, tartaric acid, bitartratic acid, ascorbic acid, succinic acid, maleic acid, besylic acid, fumaric acid, gluconic acid, glucaronic acid, formic acid, benzoic acid, glutamic acid, methanesulfonic acid, ethanesulfonic acid, benzenesulfonic acid, pamoic acid and p-toluenesulfonic acid.

A pharmaceutically acceptable carrier may contain inert ingredients which do not unduly inhibit the biological activity of the compound(s) described herein. The pharmaceutically acceptable carriers should be biocompatible, i.e., non-toxic, non-inflammatory, non-immunogenic and devoid of other undesired reactions upon the administration to a subject. Standard pharmaceutical formulation techniques can be employed, such as those described in REMINGTON, J. P., REMINGTON'S PHARMACEUTICAL SCIENCES (Mack Pub. Co., 17$^{th}$ ed., 1985). Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate, and the like. Methods for encapsulating compositions, such as in a coating of hard gelatin or cyclodextran, are known in the art. See BAKER, ET AL., CONTROLLED RELEASE OF BIOLOGICAL ACTIVE AGENTS, (John Wiley and Sons, 1986).

As used herein, the term "effective amount" refers to an amount of a compound described herein which is sufficient to reduce or ameliorate the severity, duration, progression, or onset of a disease or disorder, delay onset of a disease or disorder, retard or halt the advancement of a disease or disorder, cause the regression of a disease or disorder, prevent or delay the recurrence, development, onset or progression of a symptom associated with a disease or disorder, or enhance or improve the therapeutic effect(s) of another therapy. In an embodiment of the invention, the disease or disorder is a proliferative disorder. The precise amount of compound administered to a subject will depend on the mode of administration, the type and severity of the disease or condition and on the characteristics of the subject, such as general health, age, sex, body weight and tolerance to drugs. For example, for a proliferative disease or disorder, determination of an effective amount will also depend on the degree, severity and type of cell proliferation. The skilled artisan will be able to determine appropriate dosages depending on these and other factors. When co-administered with other therapeutic agents, e.g., when co-administered with an anti-cancer agent, an "effective amount" of any additional therapeutic agent(s) will depend on the type of drug used. Suitable dosages are known for approved therapeutic agents and can be adjusted by the skilled artisan according to the condition of the subject, the type of condition(s) being treated and the amount of a compound described herein being used. In cases where no amount is expressly noted, an effective amount should be assumed. Non-limiting examples of an effective amount of a compound described herein are provided herein below. In a specific embodiment, the method includes treating, managing, or ameliorating a disease or disorder, e.g. a proliferative disorder, or one or more symptoms thereof, comprising administering to a subject in need thereof a dose of the Hsp90 inhibitor at least 150 µg/kg, at least 250 µg/kg, at least 500 µg/kg, at least 1 mg/kg, at least 5 mg/kg, at least 10 mg/kg, at least 25 mg/kg, at least 50 mg/kg, at least 75 mg/kg, at least 100 mg/kg, at least 125 mg/kg, at least 150 mg/kg, or at least 200 mg/kg or more of one or more compounds described herein once every day, once every 2 days, once every 3 days, once every 4 days, once every 5 days, once every 6 days, once every 7 days, once every 8 days, once every 10 days, once every two weeks, once every three weeks, or once a month.

The invention can be understood more fully by reference to the following detailed description and illustrative examples, which are intended to exemplify non-limiting embodiments of the invention.

The Hsp90 inhibitors described herein can be administered to a subject by any route known to one of skill in the art. Examples of routes of administration include, but are not limited to, parenteral, e.g., intravenous, intradermal, subcutaneous, oral (e.g., inhalation), intranasal, transdermal (topical), transmucosal, and rectal administration.

The compounds described herein can be formulated into or administered by controlled release means or by delivery devices that are well known to those of ordinary skill in the art. Examples include those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566.

In general, the recommended daily dose range of an Hsp90 inhibitor for the conditions described herein lies within the range of from about 0.01 mg to about 1000 mg per day, given as a single once-a-day dose preferably as divided doses throughout a day. In one embodiment, the daily dose is administered twice daily in equally divided doses. Specifically, a daily dose range should be from about 5 mg to about 500 mg per day, more specifically, between about 10 mg and about 200 mg per day. In managing the patient, the therapy should be initiated at a lower dose, perhaps about 1 mg to about 25 mg, and increased if necessary up to about 200 mg to about 1000 mg per day as either a single dose or divided doses, depending on the patient's global response. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with individual patient response.

Different therapeutically effective amounts may be applicable for different cancers, as will be readily known by those of ordinary skill in the art. Similarly, amounts sufficient to prevent, manage, treat or ameliorate such cancers, but insufficient to cause, or sufficient to reduce, adverse effects associated with the Hsp90 inhibitors described herein are also encompassed by the above described dosage amounts and dose frequency schedules. Further, when a patient is administered multiple dosages of an Hsp90 inhibitor described herein, not all of the dosages need be the same. For example, the dosage administered to the patient may be increased to improve the prophylactic or therapeutic effect of the compound or it may be decreased to reduce one or more side effects that a particular patient is experiencing.

As use herein, an Hsp90 inhibitor-induced ocular toxicity, ocular toxicological effect, or ocular toxicity profile or visual disorder includes one or more of the following clinical symptoms:

Blurred vision
Delayed light/dark accommodation
Photophobia
Color changes
Tunnel vision
Abnormal ERG
Reversible As the first indications of clinical activity are being observed with the most clinically advanced Hsp90 inhibitory compounds, the identification of whose toxicities are dose-limiting and whether these toxicities can be managed successfully in the clinic is integral to achieving a suitable therapeutic window. It has been observed that Hsp90 inhibitors cause ocular toxicity following their administration. One possibility for this is that the modulation of Hsp90 has an effect on the rod cell-localized light-sensitive photopigment rhodopsin, which consists of opsin and a chromophore (11-cis-retinal). Opsin has been demonstrated to bind to Grp94 in the endoplasmic reticulum. As all current Hsp90 inhibitors inhibit Grp94 to varying degrees, there exists the possibility that Hsp90 inhibitors, through an inhibitory effect on Grp94, may interfere with opsin stability and cause the observed visual effects. For example, dose-dependent, low-grade visual side effects, including photophobia, blurred vision, flashes and slow dark/light adaptation were observed in a phase I, dose-escalation clinical trial with NVP-AUY922. Visual symptoms, including blurred vision, also were observed in a phase I trial with alvespimycin. No pathological findings were reported and the visual adverse effects were reversible following the discontinuation of treatment. The molecular mechanism responsible for the observed adverse effects remains unclear. However, as chaperones are expressed highly in the retina of mammals, some client proteins may be affected transiently by the modulation of Hsp90.

It is now surprisingly found that a certain concentration ratio of an Hsp90 inhibitor between retina and plasma following the administration of an Hsp90 inhibitor is indicative whether the Hsp90 inhibitor will likely cause substantial ocular toxicity. In an embodiment, a concentration ratio above 25 as measured at about 6 hours following administration of the Hsp90 inhibitor is indicative that administration of the Hsp90 inhibitor will likely induce ocular toxicity in vivo. In an embodiment, a concentration ratio of about 25 or below as measured at about 6 hours following administration of the Hsp90 inhibitor is indicative that administration of the Hsp90 inhibitor will likely have substantially less ocular toxicity in vivo. In an embodiment, a concentration ratio of about 20 or below as measured at about 6 hours following administration of the Hsp90 inhibitor is indicative that administration of the Hsp90 inhibitor will likely have substantially less ocular toxicity in vivo. In an embodiment, a concentration ratio of about 15 or below, as measured at about 6 hours following administration of the Hsp90 inhibitor, is indicative that administration of the Hsp90 inhibitor will likely have substantially less ocular toxicity in vivo. In an embodiment, a concentration ratio of about 10 or below as measured at about 6 hours following administration of the Hsp90 inhibitor is indicative that administration of the Hsp90 inhibitor will likely have substantially less ocular toxicity in vivo. In an embodiment, the subject is an animal. In an embodiment, the animal is a rat.

It is also found that the elimination rate of an Hsp90 inhibitor from the retina following the exposure of retinal tissue to the Hsp90 inhibitor is indicative whether the Hsp90 will cause significant ocular toxicity. In an embodiment, an elimination rate below 80% when measured at about half an hour and at about 6 hours following the exposure to the Hsp90 inhibitor is indicative that administration of the Hsp90 inhibitor will likely induce a toxicological effect on retinal tissue. In an embodiment, an elimination rate of about 80% or above when measured between half an hour and 6 hours following the exposure to the Hsp90 inhibitor is indicative that administration of the Hsp90 inhibitor will likely have substantially less toxicological effect on retinal tissue. In an embodiment, an elimination rate of about 85% or above when measured at about half an hour and at about 6 hours following the exposure to the Hsp90 inhibitor is indicative that administration of the Hsp90 inhibitor will likely have substantially less toxicological effect on retinal tissue. In an embodiment, an elimination rate of about 90% or above when measured at about half an hour and at about 6 hours following the exposure to the Hsp90 inhibitor is indicative that administration of the Hsp90 inhibitor will likely have substantially less toxicological effect on retinal tissue.

In an embodiment, the method includes identifying an Hsp90 inhibitor with substantially less ocular toxicity, comprising administering to a subject an effective amount of an Hsp90 inhibitor or a pharmaceutically acceptable salt or carrier thereof; determining the concentration ratio of the Hsp90 inhibitor between retina and plasma, wherein a certain concentration ratio is indicative that the Hsp90 inhibitor will have substantially less ocular toxicity.

In an embodiment, the method includes determining whether an Hsp90 inhibitor will induce ocular toxicity in vivo, comprising determining the concentration ratio of the Hsp90 inhibitor between retina and plasma following administration of the Hsp90 inhibitor to a subject, wherein a certain concentration ratio is indicative that administration of the Hsp90 inhibitor will induce ocular toxicity in vivo. In an embodiment, the concentration ratio at above 25 as measured at about 6 hours following administration of the Hsp90 inhibitor is indicative that administration of the Hsp90 inhibitor will induce ocular toxicity in vivo. In an embodiment, the concentration ratio of about concentration ratio of about 25 or below as measured at about 6 hours following administration of the Hsp90 inhibitor is indicative that administration of the Hsp90 inhibitor will have substantially less ocular toxicity in vivo. In an embodiment, the concentration ratio of about concentration ratio of about 20 or below as measured at about 6 hours following administration of the Hsp90 inhibitor is indicative that administration of the Hsp90 inhibitor will have substantially less ocular toxicity in vivo. In an embodiment, the concentration ratio of about 15 or below as measured at about 6 hours following administration of the Hsp90 inhibitor is indicative that administration of the Hsp90 inhibitor will have substantially less ocular toxicity in vivo. In an embodiment, the concentration ratio of about 10 or below as measured at about 6 hours following administration of the Hsp90 inhibitor is indicative that indicative that administration of the Hsp90 inhibitor will have substantially less ocular toxicity in vivo. In an embodiment, the subject is an animal. In an embodiment, the animal is a rat.

In an embodiment, the method includes determining whether an Hsp90 inhibitor will induce a toxicological effect on retinal tissue in vivo, the method comprising determining the elimination rate of the Hsp90 inhibitor from retina following the exposure of the retinal tissue to the Hsp90 inhibitor, wherein a certain elimination rate of the Hsp90 inhibitor is indicative that administration of the Hsp90 inhibitor will induce a toxicological effect on retinal tissue. In an embodiment, an elimination rate of below 80% when measured between half an hour and 6 hours following the exposure to the Hsp90 inhibitor is indicative that administration of the Hsp90 inhibitor will induce a toxicological effect on retinal tissue. In an embodiment, an elimination rate of about 80% or above when measured between half an hour and 6 hours following the exposure to the Hsp90 inhibitor is indicative that administration of the Hsp90 inhibitor will have substantially less toxicological effect on retinal tissue. In an embodiment, an elimination rate of about 85% or above when measured at about half an hour and at about 6 hours following the exposure to the Hsp90 inhibitor is indicative that administration of the Hsp90 inhibitor will have substantially less toxicological effect on retinal tissue. In an embodiment, an elimination rate of about 90% or above when measured at about half an hour and at about 6 hours following the exposure to the Hsp90 inhibitor is indicative that administration of the Hsp90 inhibitor will have substantially less toxicological effect on retinal tissue.

In an embodiment, the method includes identifying an Hsp90 inhibitor with substantially less ocular toxicity, the method comprising administering to a subject an effective amount of an Hsp90 inhibitor or a pharmaceutically acceptable salt or carrier thereof, and determining the concentration ratio of the Hsp90 inhibitor between retina and plasma, wherein a certain concentration ratio is indicative that administration of the Hsp90 inhibitor will cause substantially less ocular toxicity. In an embodiment, the concentration ratio is at about 25 or below as measured at about 6 hours following administration of the Hsp90 inhibitor. In an embodiment, the concentration ratio is at about 20 or below as measured at about 6 hours following administration of the Hsp90 inhibitor. In an embodiment, the concentration ratio is at about 15 or below as measured at about 6 hours following administration of the Hsp90 inhibitor. In an embodiment, the concentration ratio is at about 10 or below as measured at about 6 hours following administration of the Hsp90 inhibitor. In an embodiment, the subject is an animal. In an embodiment, the animal is a rat.

In an embodiment, the method also includes identifying an Hsp90 inhibitor with substantially less ocular toxicity, comprising administering to a subject an effective amount of an Hsp90 inhibitor or a pharmaceutically acceptable salt or carrier thereof, and determining the elimination rate of the Hsp90 inhibitor from retina, wherein a certain elimination rate indicates the Hsp90 inhibitor will cause substantially less ocular toxicity. In an embodiment, an elimination rate of 80% or above when measured at about half an hour and at about 6 hours following the exposure to the Hsp90 inhibitor is indicative that indicative that indicative that administration of the Hsp90 inhibitor will have substantially less ocular toxicity in vivoin vivo. In an embodiment, an elimination rate of about 85% or above when measured between half an hour and 6 hours following the exposure to the Hsp90 inhibitor is indicative that indicative that administration of the Hsp90 inhibitor will have substantially less ocular toxicity in vivo. In an embodiment, an elimination rate of about 90% or above when measured at about half an hour and at about 6 hours following the exposure to the Hsp90 inhibitor is indicative that indicative that administration of the Hsp90 inhibitor will have substantially less ocular toxicity in vivo. In an embodiment, the subject is an animal. In an embodiment, the animal is a rat.

In an embodiment, the method includes predicting and/or determining an ocular toxicological effect of an Hsp90 inhibitor in vivo, comprising administering to a subject an effective amount of an Hsp90 inhibitor or a pharmaceutically acceptable salt or carrier thereof, and determining the concentration ratio of the Hsp90 inhibitor between retina and plasma, wherein a certain concentration ratio of the Hsp90 inhibitor between retina and plasma is indicative that administration of the Hsp90 inhibitor will have an ocular toxicological effect in vivo. In an embodiment, the concentration ratio of about 25 or below as measured at about 6 hours following administration of the Hsp90 inhibitor is indicative that administration of the Hsp90 inhibitor will have substantially less ocular toxicity in vivo. In an embodiment, the concentration ratio of about 20 or below as measured at about 6 hours following administration of the Hsp90 inhibitor is indicative that administration of the Hsp90 inhibitor will have substantially less ocular toxicity in vivo. In an embodiment, the concentration ratio of about 15 or below as measured at about 6 hours following administration of the Hsp90 inhibitor is indicative that administration of the Hsp90 inhibitor will have substantially less ocular toxicity in vivo. In an embodiment, the concentration ratio of about concentration ratio of about 10 or below as measured at about 6 hours following administration of the Hsp90 inhibitor is indicative that administration of the Hsp90 inhibitor will have substantially less ocular toxicity in vivo. In an embodiment, the subject is an animal. In an embodiment, the animal is a rat.

In an embodiment, the invention provides a method of identifying or predicting an Hsp90 inhibitor with substantially less ocular toxicity, by administering to a subject an effective amount of an Hsp90 inhibitor or a pharmaceutically acceptable salt or carrier thereof, and determining the elimination rate of the Hsp90 inhibitor from the retina, wherein a certain elimination rate indicates the Hsp90 inhibitor will induce substantially less ocular toxicity. In an embodiment, an elimination rate of about 80% or above when measured at about half an hour and at about 6 hours following the exposure to the Hsp90 inhibitor is indicative that administration of the Hsp90 inhibitor will have substantially less ocular toxicity in vivo. In an embodiment, an elimination rate of an elimination rate of about 85% or above when measured at about half an hour and at about 6 hours following the exposure to the Hsp90 inhibitor is indicative that administration of the Hsp90 inhibitor will have substantially less ocular toxicity in vivo. In an embodiment, an elimination rate of 90% or above when measured at about half an hour and at about 6 hours following the exposure to the Hsp90 inhibitor is indicative that administration of the Hsp90 inhibitor will have substantially less ocular toxicity in vivo. In an embodiment, the subject is an animal. In an embodiment, the animal is a rat.

In an embodiment, the invention provides a method of identifying an Hsp90 inhibitor having substantially less ocular toxicity, comprising the steps of:
 a) administering to a subject an effective amount of an Hsp90 inhibitor or a pharmaceutically acceptable salt or carrier thereof;
 b) measuring the respective concentrations of the Hsp90 inhibitor in the retina and plasma;
 c) determining the concentration ratio of the Hsp90 inhibitor between retina and plasma, wherein a certain ratio is indicative that the Hsp90 inhibitor possesses substantially less ocular toxicity; and
 d) optionally, further evaluating the Hsp90 inhibitor for its therapeutic use.

In an embodiment, when the concentration ratio in step c) is at about 25% or below when step b) is performed at about 6 hours following the administration of the Hsp90 inhibitor, the Hsp90 inhibitor will likely possess substantially less ocular toxicity. In an embodiment, when the concentration ratio in step c) is at about 20% or below when step b) is performed at about 6 hours following the administration of the Hsp90 inhibitor, the Hsp90 inhibitor will likely possess substantially less ocular toxicity. In an embodiment, when the concentration ratio in step c) is at about 15% or below when step b) is performed at about 6 hours following the administration of the Hsp90 inhibitor, the Hsp90 inhibitor will likely possess substantially less ocular toxicity. In an embodiment, when the concentration ratio in step c) is at about 10% or below when step b) is performed at about 6 hours following the administration of the Hsp90 inhibitor, the Hsp90 inhibitor will likely possess substantially less ocular toxicity. In an embodiment, the subject is an animal. In an embodiment, the animal is a rat. In an embodiment, when the concentration ratio in step c) is at about 25% or below when step b) is performed at about 6 hours following the administration of the Hsp90 inhibitor, the method further comprises evaluating the Hsp90 inhibitor for its use in treating cancer. In an embodiment, when the concentration ratio in step c) is at about 25% or below when step b) is performed at about 6 hours following the administration of the Hsp90 inhibitor, the method further comprises evaluating the Hsp90 inhibitor for its use in treating melanoma. In an embodiment, when the concentration ratio in step c) is at about 25% or below when step b) is performed at about 6 hours following the administration of the Hsp90 inhibitor, the method further comprises evaluating the Hsp90 inhibitor for its use in treating non-small cell lung cancer. In an embodiment, when the concentration ratio in step c) is at about 25% or below when step b) is performed at about 6 hours following the administration of the Hsp90 inhibitor, the method further comprises evaluating the Hsp90 inhibitor for its use in treating breast cancer. In an embodiment, when the concentration ratio in step c) is at about 25% or below when step b) is performed at about 6 hours following the administration of the Hsp90 inhibitor, the method further comprises evaluating the Hsp90 inhibitor for its use in treating leukemia. In an embodiment, when the concentration ratio in step c) is at about 25% or below when step b) is performed at about 6 hours following the administration of the Hsp90 inhibitor, the method further comprises evaluating the Hsp90 inhibitor for its use in treating kidney cancer. In an embodiment, when the concentration ratio in step c) is at about 25% or below when step b) is performed at about 6 hours following the administration of the Hsp90 inhibitor, the method further comprises evaluating the Hsp90 inhibitor for its use in treating gastrointestinal stromal tumor. In an embodiment, when the concentration ratio in step c) is at about 25% or below when step b) is performed at about 6 hours following the administration of the Hsp90 inhibitor, the method further comprises evaluating the Hsp90 inhibitor for its use in treating polycystic kidney diseases. In an embodiment, when the concentration ratio in step c) is at about 25% or below when step b) is performed at about 6 hours following the administration of the Hsp90 inhibitor, the method further comprises evaluating the Hsp90 inhibitor for its use in treating an inflammatory disorder.

In an embodiment, the invention also provides a method of identifying an Hsp90 inhibitor with substantially less ocular toxicity, comprising the steps of:
  a) administering to a subject an effective amount of an Hsp90 inhibitor or a pharmaceutically acceptable salt or carrier thereof;
  b) measuring the respective concentrations of the Hsp90 inhibitor in the retina and plasma;
  c) determining the concentration ratio of the Hsp90 inhibitor between retina and plasma, wherein a certain ratio is indicative that the Hsp90 inhibitor possesses substantial less ocular toxicity; and
  d) further evaluating the Hsp90 inhibitor for its therapeutic use In an embodiment, when the concentration ration in step c) is at about 25% or below when step b) is performed at about 6 hours following the administration of the Hsp90 inhibitor, the Hsp90 inhibitor will likely possess substantially less ocular toxicity. In an embodiment, the subject is an animal. In an embodiment, the animal is a rat.

In another embodiment, the invention provides a method of identifying an Hsp90 inhibitor with substantial less ocular toxicity, the method comprising the steps of:
  a) administering to a subject an effective amount of an Hsp90 inhibitor or a pharmaceutically acceptable salt or carrier thereof;
  b) measuring the concentrations of the Hsp90 inhibitor in the retina at certain time points; and
  c) determining the elimination rate of the Hsp90 inhibitor in retina, wherein a certain elimination rate is indicative that administration of the Hsp90 inhibitor is going to cause substantially less ocular toxicity; and
  d) optionally, further evaluating the Hsp90 inhibitor for its therapeutic use.

In an embodiment, when the elimination rate of step (c) is at about 80% or more when step (b) is measured at about half hour and at about 6 hours, respectively, following the administration of the Hsp90 inhibitor, the Hsp90 inhibitor will likely possess substantially less ocular toxicity. In an embodiment, when the elimination rate of step (c) is at about 85% or more when step (b) is measured at about half hour and at about 6 hours, respectively, following the administration of the Hsp90 inhibitor, the Hsp90 inhibitor will likely possess substantially less ocular toxicity. In an embodiment, when the elimination rate of step (c) is at about 90% or more when step (b) is measured at about half hour and at about 6 hours, respectively, following the administration of the Hsp90 inhibitor, the Hsp90 inhibitor will likely possess substantially less ocular toxicity. In an embodiment, the subject is an animal. In an embodiment, the animal is a rat. In an embodiment, when the elimination rate of step (c) is at about 80% or more when step (b) is measured at about half hour and at about 6 hours, respectively, following the administration of the Hsp90 inhibitor, the method further comprises evaluating the Hsp90 inhibitor for its use in treating cancer. In an embodiment, when the elimination rate of step (c) is about 80% or more when step (b) is measured at about half hour and at about 6 hours, respectively, following the administration of the Hsp90 inhibitor, the method further comprises evaluating the Hsp90 inhibitor for its use in treating melanoma. In an embodiment, wherein the elimination rate of step (c) is at about 80% or more when step (b) is measured at about half hour and at about 6 hours, respectively, following the administration of the Hsp90 inhibitor, the method further comprises evaluating the Hsp90 inhibitor for its use in treating non-small cell lung cancer. In an embodiment, wherein the elimination rate of step (c) is at about 80% or more when step (b) is measured at about half hour and at about 6 hours, respectively, following the administration of the Hsp90 inhibitor, the method further comprises evaluating the Hsp90 inhibitor for its use in treating breast cancer. In an embodiment, wherein the elimination rate of step (c) is at about 80% or more when step (b) is measured at about half hour and at about 6 hours, respectively, following the administration of the Hsp90 inhibitor, the method further comprises evaluating the Hsp90 inhibitor for its use in treating leukemia. In an embodiment, wherein the elimination rate of step (c) is at about 80% or more when step (b) is measured at about half hour and at about 6 hours, respectively, following the administration of the Hsp90 inhibitor, the method further comprises evaluating the Hsp90 inhibitor for its use in treating kidney cancer. In an embodiment, wherein the elimination rate of step (c) is at about 80% or more when step (b) is measured at about half hour and at about 6 hours, respectively, following the administration of the Hsp90 inhibitor, the method further comprises evaluating the Hsp90 inhibitor for its use in treating gastrointestinal stromal tumor. In an embodiment, wherein the elimination rate of step (c) is at about 80% or more when step (b) is measured at about half hour and at about 6 hours, respectively, following the administration of the Hsp90 inhibitor, the method further comprises evaluating the Hsp90 inhibitor for its use in treating polycystic kidney diseases. In an embodiment, wherein the elimination rate of step (c) is at about 80% or more when step (b) is measured at about half hour and at about 6 hours, respectively, following the administration of the Hsp90 inhibitor, the method further comprises evaluating the Hsp90 inhibitor for its use in treating an inflammatory disorder.

In another embodiment, the invention also provides a method of identifying an Hsp90 inhibitor with substantial less ocular toxicity, comprising the steps of:
  a) administering to a subject an effective amount of an Hsp90 inhibitor or a pharmaceutically acceptable salt or carrier thereof;
  b) measuring the concentrations of the Hsp90 inhibitor in the retina at certain time points; and
  c) determining the elimination rate of the Hsp90 inhibitor in retina, wherein a certain elimination rate is indicative that administration of the Hsp90 inhibitor is going to cause substantially less ocular toxicity; and
  d) further evaluating the Hsp90 inhibitor for its therapeutic use.

In another embodiment, the invention also provides a method of treating a human in need thereof, comprising administering to the human an effective amount of an Hsp90 inhibitor or it pharmaceutically acceptable salt so identified as in any one of the above embodiments, wherein the administration of the Hsp90 inhibitor will cause substantially less ocular toxicity or visual disorder.

In another embodiment, the invention further provides an Hsp90 inhibitor or its pharmaceutically acceptable salt for use in treating a subject in need thereof, wherein the Hsp90 inhibitor so identified as in any one of the above embodiments will likely cause substantially less ocular toxicity or visual disorder in the subject.

In another embodiment, the invention also provides the use of an Hsp90 inhibitor or its pharmaceutically acceptable salt for the manufacture of a medicament for the treatment of a subject in need thereof, wherein the Hsp90 inhibitor so identified as in any one of the above embodiments will likely cause substantially less ocular toxicity or visual disorder in the subject.

The determination or measurement of the concentrations of the Hsp90 inhibitors in retina and plasma can be performed through routine lab equipment and experiments by a person of ordinary skill. Some of the specific procedures are illustrated in the examples shown below, which should not be limiting in any manner.

EXAMPLES

Experimental Protocol:
Animals: Male Sprague-Dawley rats or Long-Evans rats.
Treatment groups: Vehicle: D5W or DRD (10% DMSO/14%Cre-RH40/75% D5W)
17-DMAG: 10, 20, or 25 mg/kg.
17-AAG: 8, 20, 60, 100/80 mg/kg
Compound 1: 10, 20, 30, 50, 100 mg/kg
Ganetespib: 20 mg/kg
Route of Sdministration: i.v.
HER2 Degradation Assay:

HER2 positive cells were determined using anti-HER2 conjugated FITC (BD, 540553) according to manufacturer's instruction (BD Biosciences). $0.2 \times 10^6$ BT-474 cells were plated in 12-well culture plates in Dulbecco's Modified Eagle's Medium containing 10% fetal bovine serum and 1.5 g/L sodium bicarbonate. Cells were treated with the indicated compounds over a 10-1000 nM concentration range for 24 h. Cells were collected and stained with a FITC-conjugated anti-HER2 antibody for 30 min at room temperature. HER2-positive cells (fluorescence intensity) were determined by flow cytometry (excitation at 495 nm and emission at 529 nm) using a Becton Dickinson LSRII equipped with CellQuest Pro software. Half maximal inhibitory concentrations ($IC_{50}$ values) were determined based on 100% HER2 expression level of untreated control sample.

Dosing regimen: Daily for 1-3 days, or 3/week×8 doses
Tissue collection and processing:

The eyes were collected 24 hrs after the last dose, fixed in Davidson's solution for 24-48 hours, and then washed with 70-90% ethanol before routine processing for paraffin embedding and sectioning. Eye sections were stained with H&E and TUNEL. Millipore ApopTag® peroxidase in situ apoptosis detection kits were used. These kits detect apoptotic cells in situ by labeling and detecting DNA strand breaks by the TUNEL method. More particularly, ApopTag® In Situ Apoptosis Detection Kits label apoptotic cells in research samples by modifying DNA fragments utilizing terminal deoxynucleotidyl transferase (TdT) for detection of apoptotic cells by specific staining. The ApopTag® Peroxidase Kit has been qualified for use in histochemical and cytochemical staining of the following specimens: formalin-fixed, paraffin-embedded tissues, cryostat sections, cell suspensions, cytospins, and cell cultures. Whole mount-methods have been developed. The staining specificity of the ApopTag® Peroxidase Kit has been demonstrated by Chemicon and many other laboratories. Chemicon has tested many types of model cell and tissue systems, including: (a) human prostate, thymus, and large intestine (in-house data); (b) rat ventral prostate post-castration; (c) rat thymus lymphocytes treated in vitro with dexamethasone; (d) 14-day mouse embryo limbs; and (e) rat mammary gland in regression after weaning. In the thymocyte and prostate models, agarose gel electrophoresis was used to assess the amount of DNA laddering, which peaked coincidentally with the maximum percentage of stained cells. Numerous journal publications from laboratories worldwide have established the usefulness and wide applicability of ApopTag® Kits.

The histological slides were reviewed in a blind fashion by a board certified pathologist. TUNEL-stained sections were scored semi-quantitatively based on the areas and density of positive stains: (−) ≤20 cells/section, (±): minimum, (+): mild, (++): moderate, (+++): severe.

Determine Plasma and Retinal Tissue Drug Concentrations:

17-DMAG (20 mg/kg), 17-AAG (80 mg/kg), compound 1 (50 mg/kg), and ganetespib (20 mg/kg) were administered intravenously to male SD rats (n=3). The doses were selected at the level lower than MTD or mortality. Blood plasma samples were collected at 0.5 and 6 hours post-dose for bioanalysis. Retina samples were also collected at 0.5 and 6 hours post dose. Retinal samples from each time point were pooled and processed with the Covartis Cryoprep system followed by homogenization in phosphate buffered saline with an IKA homogenizer. Plasma and homogenized retinal samples were extracted by protein precipitation and analyzed by LC-MS/MS. Phenomenex Kinetex 2.6µ C18 (30×2.1 mm) column was utilized with a run time of 3.5 min per sample.

All compounds were tested in short-term studies administered i.v. at 1-3 dose levels. At necropsy, eyes were dissected and processed for histopathological examination. In subsets of animals, the retinal tissues, along with plasma and cerebrospinal fluid samples, were collected for analysis. Our results indicate that all compounds evaluated showed greater exposure in the retinal tissue compared to plasma and cerebrospinal fluid. 17-DMAG, for which visual changes have been reported in clinical subjects, produced marked photoreceptor cell death and was associated with a slow elimination rate (at 6 hrs post-dose, 50% of the drug present at 30 min remained in the retina) and a high retina/plasma (R/P) ratio. In contrast, and consistent with the absence of clinically-reported visual changes, 17-AAG at the maximum tolerated dose did not produce detectable photoreceptor injury. At 6 hr post dose, 94% of 17-AAG had been eliminated from the retina resulting in a low R/P ratio. Finally, compound 1 showed 79% drug elimination at 6 hrs and an R/P ratio that was moderately low. Photoreceptor degeneration was not observed at doses of compound 1 that were active in animal tumor models, and only minimal degeneration was seen at a higher dose. Our findings suggest that the R/P exposure ratio and elimination rate profiles play crucial roles in ocular toxicity and can be used as indicators of potential Hsp90 inhibitor-induced damage. In summary, Hsp90 plays an important role in the retina and prolonged Hsp90 inhibition can lead to vision disorders. However, ocular toxicity may be successfully minimized by administration of Hsp90 inhibitors with favorable drug properties that include, although not necessarily limited to, lower retina/plasma exposure ratios and faster retinal elimination.

Results

Table 1 shows that 17-DMAG produced ocular toxicity in rats, while 17-AAG did not induce ocular toxicity at the dose which produced mortality, nor did ganetespib at an effective dose, which is consistent with clinical observations in humans. Photoreceptor degeneration was not observed in the rats treated with compound 1 at doses that are active in animal tumor models, and only minimal-mild changes were seen at higher doses.

Table 2: shows comparison of ocular toxicity in rats treated with AUY-922, 17-DMAG, AT-13387, 17-AAG, and Compound 1. This Table includes HER2 degradation as a measure of in vitro Hsp90 inhibitory activity of each of the compounds in BT474 cells. It can be seen that unlike 17-DMAG or AUY922, 17-AAG did not induce ocular toxicity in rats, even up to doses that resulted in mortality.

Table 3 shows that the results from 17-AAG, DMAG, AYU-922, AT-13387 which are consistent with clinical observations in humans.

Table 4 shows no histopathological ocular effects were observed for ganetespib in rat and primate toxicology studies.

Table 5 shows an absence of severe common ocular toxicities in clinical studies with ganetespib.

TABLE 1

Effects of 17-DMAG, Compound 1, 17-AAG, and Ganetespib on photoreceptors in SD rats

| Compound | HER2 degradation IC50 (nM) | Treatment Doses (mg/kg, i.v.) | Retina/plasma conc. | Total # of rats | Photoreceptor degeneration/ apoptosis | Toxicity |
|---|---|---|---|---|---|---|
| Vehicle | — | 10 ml/kg | — | >10 | (−) (±) occasionally | — |
| 17-AAG | 100-150 | 8, 20, 60 | — | 9 | (−) | Mortality: 100 mg/kg |
|  |  | 80 (100) | Examined | 6 | (−) |  |
| Compound 1 | 60 | 10, 20, 30 | — | 9 | (−) | MTD: 100 mg/kg |
|  |  | 50 | Examined | 3 | (±) |  |
|  |  | 100 | — | 3 | (±-+) |  |
| 17-DMAG | 60 | 10 | — | 6 | (±-++) | Mortality: 25 mg/kg/dx 3 days |
|  |  | 20 (25) | Examined | 9 | (+-+++) |  |
| Ganetespib | 30 | 20 | Examined | 7 | (−) | Cmax & AUCt > human dose |
| AUY922 | 30 | 3 | — | 3 | (−) | No mortality in 2-3 days post-dose |
|  |  | 10 | Examined | 3 | (+-++) |  |
|  |  | 30, 60 | — | 6 | (+_++++) |  |

TABLE 2

Comparison of ocular toxicity in rats treated with AUY-922, 17-DMAG, AT-13387, 17-AAG, and Compound 1

| TA | HER2 IC50(nM) | Species | Testing doses(mg/kg/ dx2, iv.) | Incidences (#affected/total) | Severity (TUNEL + area & density) | Mortality (in-house study) |
|---|---|---|---|---|---|---|
| AUY-922 (Novartis) | <30 | SD rats | 3 | 0/3 | (−) | 0/12 (others: tail edema, ↓ Body weight gain) |
|  |  |  | 10 & 30 | 6/6 | (+-++) |  |
|  |  |  | 60 | 3/3 | (+-+++) |  |
| 17-DMAG | 60 | SD rats | 10 | 3/3 | (±-++) | 3/3 @ 25 mg/kg/dx3_72 hrs |
|  |  |  | 20, 25 | 6/6 | (+-++) |  |
| AT-13387 (Astex) |  | SD rats | 10 | 0/3 | (−) | 0/9 (↓ Body weight gain) |
|  |  |  | 30 | 0/3 | (−) |  |
|  |  |  | 60 | 2/3 | 2/3 (++-+++) |  |
|  |  |  | 3 | 6/6 | (±-+++) |  |
|  |  |  | 10 | 6/6 | (±-+) |  |
| compound 1 | 60 | SD rats | 10 | 0/3 | (−) | 0/15 (ECG change @ 100 mg/kg) |
|  |  |  | 20 | 0/3 | (−) |  |
|  |  |  | 30 | 0/3 | (−) (1/3±, 22 cells/section) |  |
|  |  |  | 50 | 3/3 | (±) |  |
|  |  |  | 100 | 3/3 | (±-+) |  |
| 17-AAG | 100-150 | SD rats | 8, 20, 60, 100/80 | 0/10 | (−) | 1/3; 100 mg/kg in 5 min, 1/1: 120 mg/kg in 5 min. |

Histological score: (−) ≤ 20 cells/section, (±) 21-30 cells/section, (+) <30%, (++) 30-60%, (+++) <60% area

TABLE 3

Summary of Hsp90i distribution in the retina of SD rats

| TA | Dose (mg/kg) | TUNEL | Day | Time (h) | Plasma (μM) | Retina (μM) | CSF (μM) | R/P ratio | Retina %↓ 0.5-6 h (% remain) |
|---|---|---|---|---|---|---|---|---|---|
| AUY922 | 10 | +-++ | 2 | 0.5 | 1.12 | 4.75 | BQL | 4.24 | 46.5 |
|  |  |  |  | 6 | 0.0154 | 2.54 | BQL | 165 | (53.5) |

TABLE 3-continued

Summary of Hsp90i distribution in the retina of SD rats

| TA | Dose (mg/kg) | TUNEL | Day | Time (h) | Plasma (µM) | Retina (µM) | CSF (µM) | R/P ratio | Retina %↓ 0.5-6 h (% remain) |
|---|---|---|---|---|---|---|---|---|---|
| 17-DMAG | 20 | +-++ | 2 | 0.5 | 4.71 | 32.0 | 0.0799 | 6.79 | 49.4 |
|  |  |  |  | 6 | 0.317 | 16.2 | 0.00376 | 51.1 | (50.6) |
| Compound 1 | 50 | ± | 2 | 0.5 | 19.5 | 10.4 | 0.0194 | 0.53 | 78.5 |
|  |  |  |  | 6 | 0.104 | 2.24 | BQL | 21.5 | (21.5) |
| 17-AAG | 80 | (−) | 2 | 0.5 | 26.5 | 45.1 | 0.434 | 1.70 | 94.4 |
|  |  |  |  | 6 | 0.262 | 2.51 | 0.00433 | 9.58 | (5.6) |

TABLE 4

Ganetespib administered by 1 h i.v. infusion on days 1 and 15 over four 21-day cycles did not cause histopathological changes in the retina of rats or cynomolgus monkeys.

| Compound | Testing species (M + F) | Max. Dose levels (mg/kg) | Route | Regimen | Ocular histopathology evaluation |
|---|---|---|---|---|---|
| ganetespib | SD rats | 100* | i.v. | Days 1 & 15 of four 21-day cycles Total 3-month | No changes |
|  | Monkeys | 7** | 1 hour infusion |  | No changes |

*Formulated with 10% DMSO/14% Cre-RH40/75% D5W
**Formulated with 2% Dehydrated alcohol/3.15% PEG 300/2.8% Tween 80/D5W

TABLE 5

All adverse events were either mild or moderate and transitory

| Ganetespib | All adverse events | | Related adverse events | |
|---|---|---|---|---|
| (n = 390) | Grade 1 | Grade 2 | Grade 1 | Grade 2 |
| Vision blurred | 11 (3%) | 2 (<1%) | 4 (1%) | — |
| Visual impairment | 5 (1%) | — | 2 (<1%) | — |
| Visual acuity reduced | 2 (<1%) | — | 1 (<1%) | — |
| Chromatopsia | 1 (<1%) | — | 1 (<1%) | — |
| Difficulty with night vision | 1 (<1%) | — | — | — |

It can be seen from these experiments that Hsp90 plays an important role in retinal function; that prolonged Hsp90 inhibition can lead to vision disorders; that ocular toxicity detected in rats treated with 17-DMAG, but not with 17-AAG or ganetespib, were consistent with the visual clinical findings in humans; that the profiles of retinal/plasma exposure ratio and elimination rate play crucial roles in ocular toxicity and can be used as indicators of potential Hsp90 inhibitor-induced retinal damage in rats; and that ocular toxicity may be successfully minimized by administration of Hsp90 inhibitors with favorable drug properties that include, although not necessarily limited to, lower retina/plasma exposure ratios and faster retinal elimination.

REFERENCES

1. *Heat Shock Protein* 90 *Inhibitors Can Induce Visual Changes And Retinal Degeneration Including Irreversible Photoreceptor Loss In Dogs.* V. Torti; J. Marcek; K. Muravnick; S. Aguirre; J. Fortner; J. Render; T. Schmahai; S. Yamazaki; L. Nguyen; Z. Shen; L. Burns-Naas. Abstract, 2011 *Society of Toxicology Annual Meeting*
2. *Hsp*90 *Inhibitors Reduce Electroretinogram Responses In Dogs.* C. Somps; C. Liu; N. Poy; J. Marcek; V. Torti. Abstract, 2011 *Society of Toxicology Annual Meeting*

All publications, patent applications, patents, and other documents cited herein are incorporated by reference in their entirety. In case of conflict, the present specification, including definitions, will control. In addition, the materials, methods, and examples throughout the specification are illustrative only and not intended to be limiting in any way.

What is claimed is:

1. A method of determining whether an Hsp90 inhibitor will induce a toxicological effect on retinal tissue, comprising determining the elimination rate of an Hsp90 inhibitor from retina following the exposure of the retinal tissue to the Hsp90 inhibitor, where a certain elimination rate of the Hsp90 inhibitor is indicative that administration of the Hsp90 inhibitor will not induce a toxicological effect on retinal tissue.

2. The method of claim 1, where the elimination rate of about 80% or above as measured at about half an hour and at about 6 hours following the exposure of retinal tissue to the Hsp90 inhibitor is an indication that the Hsp90 inhibitor will not induce a toxicological effect on the retinal tissue.

3. A method of identifying an Hsp90 inhibitor with substantially less ocular toxicity, comprising administering to a subject an effective amount of an Hsp90 inhibitor or a pharmaceutically acceptable salt or carrier thereof, and determining the elimination rate of the Hsp90 inhibitor from retina, wherein a certain elimination rate indicates the Hsp90 inhibitor will cause substantially less ocular toxicity.

4. A method of predicting an ocular toxicological effect of an Hsp90 inhibitor, comprising administering to a subject an effective amount of an Hsp90 inhibitor or a pharmaceutically acceptable salt or carrier thereof, and determining the elimination rate of the Hsp90 inhibitor from retina, wherein a certain elimination rate is indicative that administration of the Hsp90 inhibitor will have an ocular toxicological effect.

5. A method of identifying an Hsp90 inhibitor with substantially less ocular toxicity, comprising the steps of:

a) administering to a subject an effective amount of an Hsp90 inhibitor or a pharmaceutically acceptable salt or carrier thereof;
b) measuring the concentrations of the Hsp90 inhibitor in the retina at certain time points; and
c) determining the elimination rate of the Hsp90 inhibitor from retina, wherein a certain elimination rate is indicative that administration of the Hsp90 inhibitor will induce substantially less ocular toxicity; and
d) optionally, further evaluating the Hsp90 inhibitor for its therapeutic use.

6. The method of claim 5, wherein an elimination rate of about 80% or above as measured at about half hour and at about 6 hours following the administration of the Hsp90 inhibitor in an indication that the Hsp90 inhibitor will have substantially less ocular toxicity, and the method further comprising evaluating the Hsp90 inhibitor for its anticancer utility.

7. The method of claim 5, wherein the subject is an animal.

8. The method of claim 7, wherein the animal is a rat.

* * * * *